(12) United States Patent
Li et al.

(10) Patent No.: US 9,955,945 B2
(45) Date of Patent: May 1, 2018

(54) METHODS AND SYSTEMS FOR BROADBAND INTRAVASCULAR ULTRASOUND IMAGING

(71) Applicant: General Electric Company, Schenectady, NY (US)

(72) Inventors: Xiang Li, Niskayuna, NY (US); Ying Fan, Niskayuna, NY (US); Hao Lai, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 281 days.

(21) Appl. No.: 14/479,743

(22) Filed: Sep. 8, 2014

(65) Prior Publication Data
US 2016/0066881 A1    Mar. 10, 2016

(51) Int. Cl.
| | | |
|---|---|---|
| *A61B 8/12* | (2006.01) | |
| *G01S 15/89* | (2006.01) | |
| *B06B 1/02* | (2006.01) | |
| *B06B 1/06* | (2006.01) | |
| *A61B 8/00* | (2006.01) | |
| *A61B 8/08* | (2006.01) | |

(52) U.S. Cl.
CPC .............. *A61B 8/12* (2013.01); *A61B 8/0891* (2013.01); *B06B 1/0215* (2013.01); *B06B 1/0622* (2013.01); *G01S 15/8954* (2013.01); *G01S 15/8961* (2013.01); *A61B 8/4483* (2013.01); *A61B 8/5207* (2013.01); *A61B 8/54* (2013.01); *B06B 2201/55* (2013.01); *B06B 2201/76* (2013.01)

(58) Field of Classification Search
CPC .................................. A61B 8/00; B06B 1/00
See application file for complete search history.

(56) References Cited

U.S. PATENT DOCUMENTS

| | | |
|---|---|---|
| 7,396,332 B2 | 7/2008 | Taimisto et al. |
| 8,298,149 B2 | 10/2012 | Hastings et al. |
| 8,345,513 B2 | 1/2013 | Huang |
| 8,396,276 B2 | 3/2013 | Gatta et al. |

(Continued)

OTHER PUBLICATIONS

"Estimation of ultrasonic attenuation in a bone using coded excitation" by A. Nowicki et al. Ultrasonics. 41 (2003) 615-621.*

(Continued)

*Primary Examiner* — Tse Chen
*Assistant Examiner* — Jason Ip
(74) *Attorney, Agent, or Firm* — Pabitra K. Chakrabarti

(57) ABSTRACT

An ultrasound imaging system, a method for ultrasound imaging and a non-transitory computer readable medium that stores instructions executable by one or more processors to perform the method for ultrasound imaging are presented. The method includes convolving one or more base ultrasound pulses corresponding to a particular frequency with a desired code to generate an extended excitation wave. Further, the extended excitation wave is transmitted to a broadband ultrasound transducer to be transmitted towards the target. Subsequently, echo signals reflected back from the target in response to the extended excitation wave are received and de-convolved. One or more ultrasound images of the target corresponding to multiple frequencies are generated based on the de-convolved echo signals.

19 Claims, 4 Drawing Sheets

(56) References Cited

U.S. PATENT DOCUMENTS

| | | | |
|---|---|---|---|
| 2003/0149361 A1* | 8/2003 | Miwa | G01S 15/895 |
| | | | 600/437 |
| 2008/0125658 A1* | 5/2008 | Lee | A61B 8/12 |
| | | | 600/459 |
| 2009/0024040 A1 | 1/2009 | Cespedes | |
| 2009/0209858 A1* | 8/2009 | Oelze | G01S 7/52077 |
| | | | 600/443 |
| 2010/0076318 A1 | 3/2010 | Rehrig et al. | |
| 2010/0160788 A1 | 6/2010 | Davies et al. | |
| 2011/0016058 A1 | 1/2011 | Pinchuk | |
| 2011/0087104 A1 | 4/2011 | Moore et al. | |
| 2011/0160586 A1* | 6/2011 | Li | A61B 5/02007 |
| | | | 600/443 |

OTHER PUBLICATIONS

"Pulse Elongation and Deconvolution Filtering for Medical Ultrasonic Imaging" by B. Haider. IEEE Trans Ultra Ferr Freq Cntrl. vol. 45, No. 1, Jan. 1998 pp. 98-113.*

Yeh et al., "High-frequency CMUT arrays for high-resolution medical imaging", SPIE Digital Library, vol. 5750, Jun. 3, 2005, 12 Pages.

Wenguang Li et al., "Multi-frequency processing for lumen enhancement with wideband intravascular ultrasound", Ultrasonics Symposium, 2008. IUS 2008. IEEE, pp. 371-374, Nov. 2008.

Xiang Li et al., "Ultrasound Transducer and Method for Manufacturing an Ultrasound Transducer", U.S. Appl. No. 14/068,338, filed Oct. 31, 2013, 40 Pages.

* cited by examiner

METHODS AND SYSTEMS FOR BROADBAND INTRAVASCULAR ULTRASOUND IMAGING

BACKGROUND

Embodiments of the present specification relate generally to interventional procedures, and more particularly to methods and system for improved broadband intravascular ultrasound imaging.

Interventional techniques are widely used for managing a plurality of life-threatening medical conditions. Particularly, certain interventional techniques entail minimally invasive image-guided procedures that provide a cost-effective alternative to invasive surgery. For example, intravascular ultrasound (IVUS) imaging may be used for diagnosing and/or treating diseased blood vessels using image-derived information. Specifically, IVUS imaging may be used to ascertain existence and progression of atherosclerosis plaques, narrowing of the lumen, and/or intracoronary thrombosis that may lead to a heart attack, stroke, and/or cardiac death.

Generally, IVUS imaging systems used in such diagnoses employ a miniaturized ultrasound probe including a catheter having a diameter of less than about 1.2 millimeter (mm). The IVUS catheter may be inserted into, or proximal, a region of interest (ROI) such as a coronary vessel for visualizing structural aspects of the vessel in offline or real-time mode. Particularly, the IVUS catheter may include an imaging sensor such as a side-looking ultrasound transducer that may be used to generate cross-sectional images from within the vessel.

Conventional ultrasound transducers used for generating the cross-sectional images operate between center frequencies of about 20 MegaHertz (MHz) and about 45 MHz with an imaging bandwidth approximately between 30-50 percent. However, conventional ultrasound transducers may provide insufficient resolution for imaging specific features of a subject. For example, use of the center frequencies between 20-40 MHz and the imaging bandwidth between 30-50 percent may provide insufficient resolution for evaluating the vulnerability of atherosclerotic plaques with relatively thin fibrous caps, for example, having a thickness of less than approximately 64 micrometers ($\mu$m).

Accordingly, an ultrasound transducer having higher resolution may be preferred to diagnose diseased regions of a patient. However, IVUS imaging resolution is inversely proportional to a frequency bandwidth of the transducer. Typically, a transducer with broad bandwidth and higher working frequency is able to generate short ultrasonic pulses that are useful in distinguishing close targets in an axial direction. However, use of higher frequencies results in higher ultrasound attenuation, which in turn, results in lower penetration depth. Alternatively, a transducer operating at lower frequencies may provide greater penetration depth, but may not provide sufficient image resolution.

Conventional interventional procedures, thus, may entail use of different ultrasound transducers, one or more of which may operate at high frequencies to provide images having higher resolution, while others operate at lower frequencies to provide greater penetration depth. Alternatively, additional imaging modalities such as optical coherence tomography system or a fluorescence system may be employed to determine either high resolution or depth-based information. Use of different imaging modalities and/or different ultrasound transducers, however, prolongs imaging time, while adding to the equipment and operational costs. Furthermore, integrating two different transducers to the tip of a catheter having less than 1 mm diameter causes complicated packaging problems.

BRIEF DESCRIPTION

In accordance with aspects of the present specification, an ultrasound imaging is disclosed. The system includes a broadband ultrasound transducer configured to transmit ultrasound pulses towards a target and a processing subsystem operatively coupled to the broadband ultrasound transducer. The processing subsystem is configured to convolve one or more base ultrasound pulses corresponding to a particular frequency with a desired code to generate an extended excitation wave. Further, the processing subsystem is configured to transmit the extended excitation wave to the broadband ultrasound transducer to be transmitted towards the target. Additionally, the processing subsystem is configured to receive echo signals reflected back from the target in response to the extended excitation wave and de-convolve the received echo signals. The processing subsystem is also configured to generate one or more ultrasound images of the target corresponding to multiple frequencies based on the de-convolved echo signals.

In accordance with further aspects of the present specification, a method for ultrasound imaging and a non-transitory computer readable medium that stores instructions executable by one or more processors to perform the method for ultrasound imaging are presented. The method includes convolving one or more base ultrasound pulses corresponding to a particular frequency with a desired code to generate an extended excitation wave. Further, the extended excitation wave is transmitted to a broadband ultrasound transducer to be transmitted towards the target. Subsequently, echo signals reflected back from the target in response to the extended excitation wave are received and de-convolved. One or more ultrasound images of the target corresponding to multiple frequencies are then generated based on the de-convolved echo signals.

A technical effect of the present specification includes use of a broadband ultrasound transducer including a micromachined piezoelectric composite body to allow for increased bandwidth, increased sensitivity, and/or reduced acoustic impedance during intravascular ultrasound (IVUS) imaging. Particularly, use of the micromachined piezoelectric composite body allows the transducer to provide relatively high definition tissue imaging with a relatively large dynamic range, and a relatively deep penetration depth when compared to conventional ultrasound systems. Additionally, embodiments of the present specification present methods for coded excitation of the ultrasound transducer that leverages the broadband imaging capabilities of the ultrasound transducer to generate high quality images that may aid in accurate diagnosis.

DRAWINGS

These and other features, aspects, and advantages of the present specification will become better understood when the following detailed description is read with reference to the accompanying drawings in which like characters represent like parts throughout the drawings, wherein.

DETAILED DESCRIPTION

The following description presents methods and systems for broadband intravascular ultrasound (IVUS) imaging using coded excitation. Particularly, certain embodiments illustrated herein describe methods and systems that use a broadband ultrasound transducer including a micromachined piezoelectric composite material and a dematching layer. The micromachined piezoelectric composite material allows the transducer to operate at a greater bandwidth, greater sensitivity, and lower acoustic impedance. Further, the dematching layer aids in increasing a power of the ultrasound waves transmitted to a face layer of a lens to enhance multi-frequency imaging capabilities of the broadband ultrasound transducer. Additionally, the embodiments described herein disclose use of a coded excitation sequence that leverages the broadband capabilities of the transducer to provide clinically suitable images having both high resolution and a deep penetration depth.

Although the following description is discussed with reference to IVUS imaging, certain embodiments of the present methods and systems may also be implemented in connection with other types of ultrasound systems, such as transesophageal echocardiography (TEE) systems and/or Intra-Cardiac Echocardiography (ICE) systems. Furthermore, the methods and systems described herein may find use, for example, in improving detection of coronary artery lesion and other anomalies in heart, thyroid, liver, or other organs of a subject.

In certain embodiments, the present systems and methods may be used for non-medical purposes, such as for nondestructive testing of fluid delivery systems, assessing leaks and blockages, and/or estimating differential pressure in pipes and/or other non-biological objects. Additionally, embodiments of the present specification may also be implemented in electromagnetic, electrochemical, electromechanical, electro-optical, radio-acoustic, and/or any other application area where a broadband transducer may be used. An exemplary environment that is suitable for practicing various implementations of the present system will be described in the following sections with reference to FIG. 1.

Figure 1:
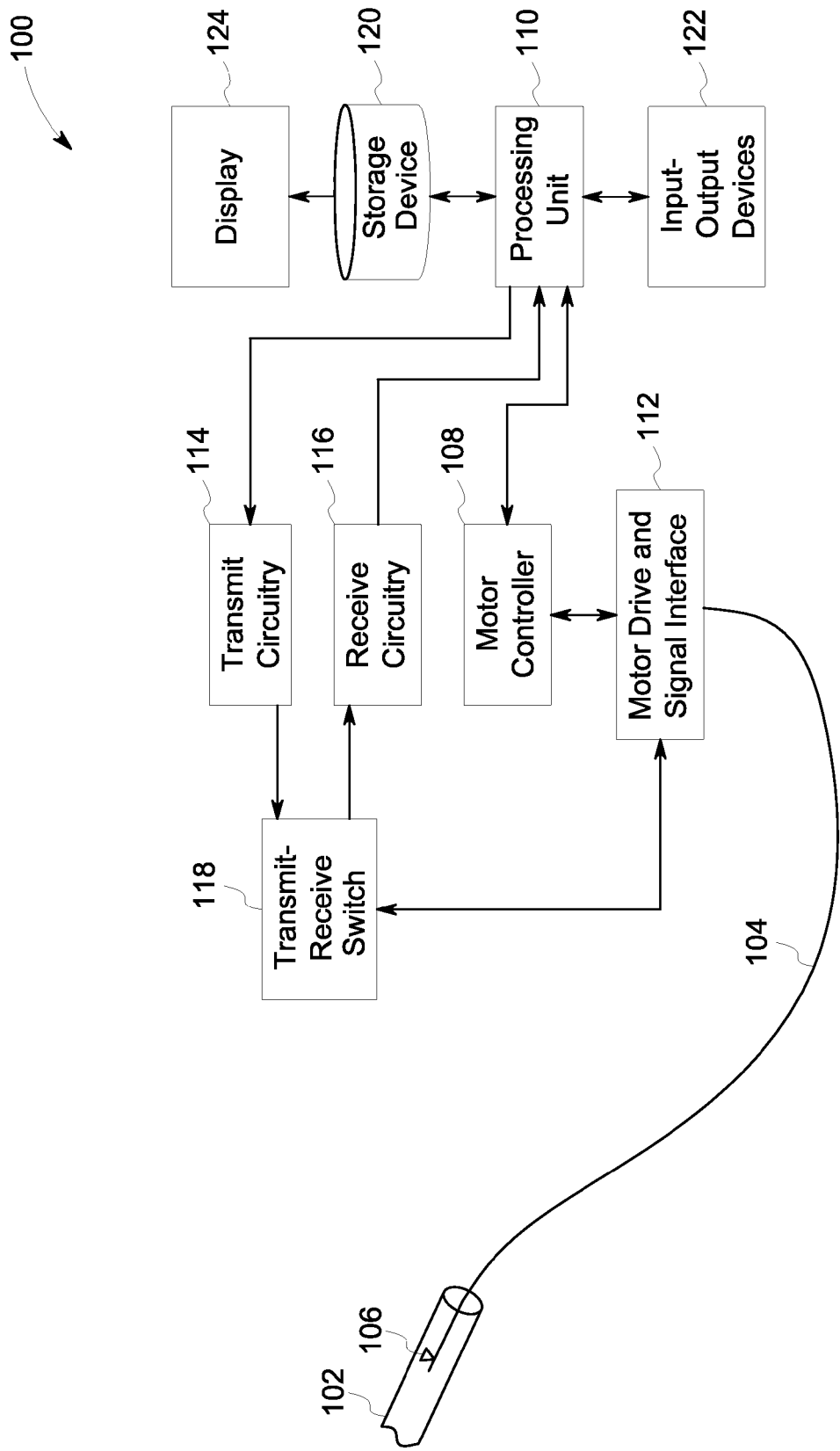
FIG. 1 is a schematic representation of an exemplary imaging system for broadband intravascular ultrasound (IVUS) imaging, in accordance with aspects of the present specification.

FIG. 1 illustrates an exemplary IVUS imaging system 100. In one embodiment, the system 100 may be configured for imaging, providing a functional evaluation, and/or for providing therapy to one or more target regions in biological tissues and/or non-biological objects of interest. For discussion purposes, the system 100 is described with reference to an IVUS system for use in diagnosing and/or providing treatment to a patient. However, as previously noted, in certain embodiments, the system 100 may also be implemented in other medical and/or non-medical systems such as ultrasound biomicroscopy system, photoacoustic imaging system, nondestructive evaluation system, etc.

In one embodiment, the system 100 includes an interventional device such as a catheter 104 adapted for use in a confined medical or surgical environment such as a body cavity, orifice, or the blood vessel 102. The catheter 104 may further include at least one image sensor such as a side-looking and/or forward-looking broadband transducer 106. In certain embodiments, the transducer 106 corresponds to a single element broadband transducer. Further, the transducer 106 is disposed at a distal end of the catheter 104 and is configured to generate two or more images corresponding to different frequencies at the same time and for the same cross section of the blood vessel 102. The transducer 106, thus, allows for multi-frequency IVUS imaging without use of a second transducer and/or an additional imaging modality.

To that end, in one embodiment, the transducer 106 includes an acoustic layer of a micromachined piezoelectric composite material having a broad frequency response. Particularly, in one example, the frequency response of the transducer 106 may cover approximately 35-85 MHz (at an intensity of about −6 decibels (dB)) or approximately 15-120 MHz (at an intensity of about −40 dB) of frequency range. Additionally, the micromachined piezoelectric composite material may have a relatively high electromechanical coupling coefficient and relatively low acoustic impedance to facilitate multi-frequency IVUS imaging. The high coupling coefficient and low acoustic impedance of the piezoelectric composite material result in lower acoustic reverberation, thereby allowing for greater sensitivity and/or bandwidth of the transducer 106. Certain exemplary structural and functional aspects of the broadband transducer 106 will be described in greater detail with reference to FIG. 4.

In one embodiment, the catheter 104 including the transducer 106 is inserted into the target blood vessel 102 through one or more small incisions for reducing patient recovery time. In certain embodiments, the transducer 106 is configured to rotate inside the blood vessel 102 for generating corresponding cross-sectional images under control of a motor controller 108 and/or a processing subsystem 110 via a motor drive and signal interface 112. Additionally, the motor controller 108 and/or the processing subsystem 110 may also control operation of the transducer 106 to generate excitation pulses of a desired frequency and/or repetition rate for use in estimating tissue characteristics.

Figure 2:
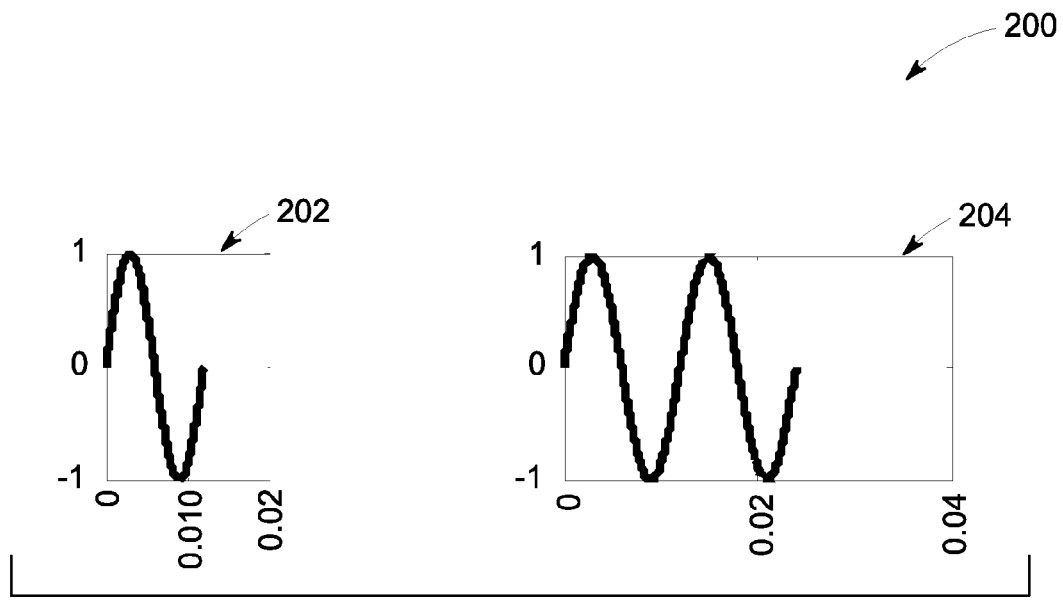
FIG. 2 is a graphical representation of conventional excitation pulses used in conventional IVUS imaging.

Conventional IVUS systems employ only single or two cycles of excitation pulses for imaging a target feature at a single frequency. FIG. 2, for example, illustrates a graphical representation 200 depicting examples of conventional excitation pulses 202 and 204. As depicted in FIG. 2, the excitation pulses 202 and 204 include only one and two cycles of sinusoidal waves, respectively. As previously noted, use of the conventional excitation pulses having a single frequency may fail to provide sufficient image resolution and penetration depth simultaneously in the same or different images.

Accordingly, with returning reference to FIG. 1, embodiments of the system 100 employ a coded excitation sequence to leverage the multi-frequency IVUS imaging capability of the transducer 106. Although coded excitation has been used in RADAR and SONAR applications, coded excitation of a conventional IVUS transducer results in unacceptably high-range side lobes due to limited bandwidth of a conventional ultrasound transducer. Thus, coded excitation is typically unfeasible for use in conventional low-bandwidth IVUS imaging.

In contrast, use of coded excitation with an embodiment of the broadband transducer 106 of FIG. 1 significantly improves a signal-to-noise (SNR) ratio without either increasing the peak transmitted power or sacrificing resolution of resulting IVUS images. Accordingly, in one embodiment, the processing subsystem 110 is configured to determine one or more desired codes for convolving the excitation pulses. The desired codes, for example, may include Barker codes, Golay codes, Chirp Codes, and/or other suitable codes designed for specific imaging applications. In one embodiment, the desired codes may be pre-programmed into the system 100, selected from a plurality of suitable codes based on a stored correlation, and/or may be input by a user prior to or during ultrasound imaging.

In certain embodiments, the desired codes suitable for a particular imaging application may be selected based on a desired working frequency and energy requirement. Alternatively, or additionally, the desired codes may be selected to achieve a desired tradeoff of coded-excitation induced artifacts such as range side lobes and ultrasound main-band convolution. To that end, in one embodiment, a correlation between desired imaging parameters such as the working frequency and energy specifications, and desired tradeoff parameters may be defined and stored in the storage device 120 for different applications. Subsequently, the processing subsystem 110 may be configured to use the stored correlation to select the desired code during ultrasound imaging automatically or via user selection.

Further, the processing subsystem 110 may be configured to use the desired code for convolving base excitation pulses to allow for multi-frequency IVUS imaging. Particularly, in one embodiment, the processing subsystem 110 may be configured to direct a transmit circuitry 114 in the system 100 to convolve base excitation pulses, such as one or two cycles of sinusoidal waves at a particular frequency, using the desired code.

As used herein, the term "convolve" and any variations thereof may be used in the present specification to refer to a method for processing ultrasound signals to generate an extended or coded excitation signal, where the processing includes modulation, encoding, concatenation, and/or convolution. Specifically, in one embodiment, convolving the ultrasound pulses may entail determining an integral that expresses an amount of overlap of one function (for example, a first ultrasound signal) as it is shifted over another function (for example, a second ultrasound signal), thereby "blending" one function with another. For example, in an implementation, one or more of the base excitation pulses may be combined and/or undergo a change in phase to generate an extended excitation pulse that embeds the desired code.

Figure 3:
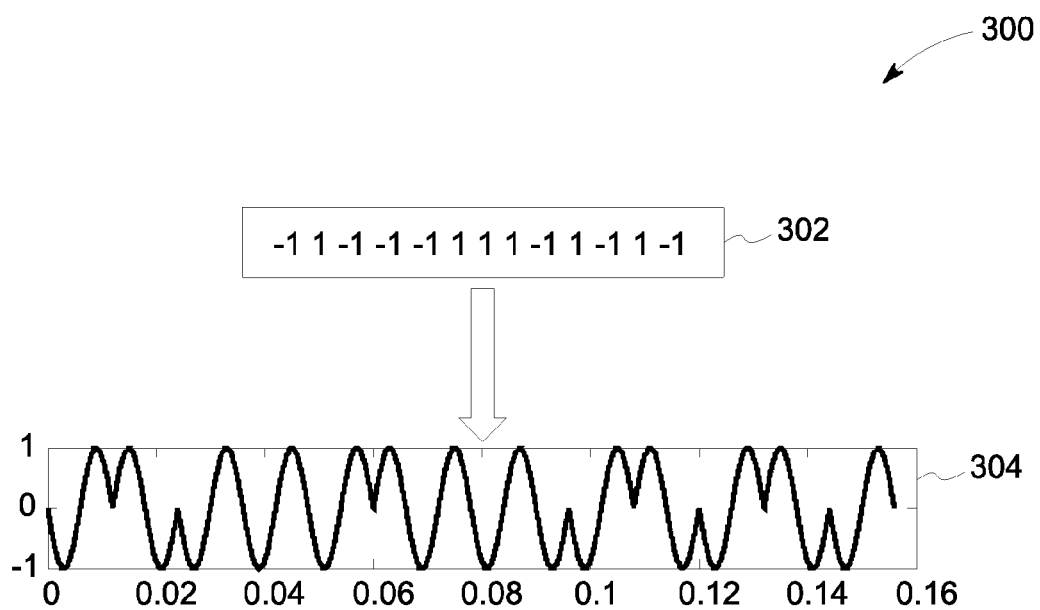
FIG. 3 is a graphical representation of exemplary coded excitation pulses used for broadband IVUS imaging, in accordance with aspects of the present specification.

FIG. 3 illustrates a graphical representation 300 of exemplary extended excitation pulse used for broadband IVUS imaging. FIG. 3 shows an example of a determined sequence of a desired code 302 that may be pre-programmed into the system 100, selected from a predetermined list, and/or input by the user. In one embodiment, the code sequence 302 may be used to combine and convolve base excitation pulses at a single frequency, such as the pulses 202 and 204 depicted in FIG. 2, into an extended excitation pulse 304.

In certain embodiments, the extended excitation pulse may be generated in single and/or tone bursts and may be unipolar, bipolar, and/or arbitrary pulses having application-defined or user-defined duration and/or frequency. In one embodiment, the extended excitation pulse increases a total energy transmitted into a target region before reaching a specified intensity limit, thereby increasing a penetration depth and/or signal-to-noise-ratio (SNR). Specifically, the extended excitation pulse allows for an increase in the energy transmitted to the target region without causing any significant loss in image resolution. Although, use of the extended excitation pulse benefits ultrasound imaging at all frequencies, the extended excitation pulses significantly improve penetration depth and SNR at higher frequencies. Accordingly, in one embodiment, the extended excitation pulse may be used to drive the broadband transducer 106 of FIG. 1 at multiple frequency bands, for example at about 40 MHz, about 60 MHz, and/or about 80 MHz, for imaging a target region such as a suspected atherosclerotic lesion.

With returning reference to FIG. 1, in one embodiment, at least a portion of the extended excitation signal is reflected from the target region to the transducer 106. The transducer 106 may convert the reflected ultrasound signals into electrical signals that may pass through the motor drive and signal interface 112 and/or a transmit-receive switch 118 to receive circuitry 116 for further processing. In certain embodiments, the receive circuitry 116 communicates the received electrical signals to the processing subsystem 110 that processes the received signals according to a plurality of selectable ultrasound modalities in real-time and/or off-line mode. For example, the processing subsystem 110 may pre-amplify, digitize, and/or evaluate the received signals for determining clinically useful indicators.

Specifically, the processing subsystem 110 may be configured to de-convolve or decode the received signals to recover an original resolution of the transducer 106. As used herein, the term "de-convolve" and variations thereof may be used to refer to a method of reversing effects of convolution on the received ultrasound pulses, where de-convolving may include demodulation, decoding, decoupling, and/or de-convolution. By way of example, the received ultrasound pulses may be de-convolved using statistical estimation, wavelet-based de-convolution, filter-based de-convolution, envelope-based de-convolution, and/or by using any other suitable technique.

In certain embodiments, the processing subsystem 110 may process and/or de-convolve the received signals at different frequencies so as to reconstruct multiple two-dimensional (2D) and/or a three-dimensional (3D) cross-sectional image of the same cross-section of the target region at the different resolutions and desired penetration depths. To that end, in certain embodiments, the processing subsystem 110 includes devices such as one or more application-specific processors, digital signal processors, microcomputers, microcontrollers, Application Specific Integrated Circuits (ASICs) and/or Field Programmable Gate Arrays (FPGAs). The processing subsystem 110 may also include suitable devices capable of communicating with other components of the system 100 such as a picture archiving and communications system (PACS), a radiology department information system, hospital information system and/or to an internal or external communications network (not shown).

In certain embodiments, the processing subsystem 110 stores the received signals, the processed information, and/or the reconstructed images along with the desired code, delivery sequence, repetition frequency, time delay, intensity, imaging system parameters, and/or other operational data in a storage device 120. The storage device 120, for example, may include devices such as a random access memory, a read-only memory, a disc drive, a solid-state memory device, and/or a flash memory. In certain embodiments, the storage device 120 may also store the desired code, commands, and inputs received from an operator during the interventional procedure.

Further, in one embodiment, the processing subsystem 110 may be coupled to one or more user input-output devices 122, such as a keyboard, touchscreen, microphone, mouse, buttons, switches, audio devices, and/or video devices. The input-output devices 122 may be configured to receive operator input, desired codes, and commands, and/or output the reconstructed images and processed information from the user and/or the processing subsystem 110. Particularly, in one embodiment, the processing subsystem 110 allows the operator to input and/or select the desired codes, one or more ROIs and/or imaging parameters using a graphical user interface on a local or remote display device 124.

In certain embodiments, the processing subsystem 110 is configured to display the 2D and/or 3D images along with clinically useful information such as patient data on the display device 124. The displayed information aids in in review, diagnosis, analysis, and/or treatment of the patient. Particularly, in one embodiment, the processing subsystem 110 simultaneously displays the 2D and/or 3D images that are reconstructed from the same set of received signals and are indicative of high resolution and desired depth-based information corresponding to the target region. In a further embodiment, the processing subsystem 110 stores the 2D and/or 3D images and the clinically useful information for later review and analysis, and/or communicates the images and clinically useful information to a remotely located medical practitioner for further evaluation.

In certain embodiments, the 2D and/or 3D images including the high resolution and desired depth-based information may be used for determining structural characteristics corresponding to the target region with greater accuracy. For example, the images may be used to identify locations and tissue morphology of an atherosclerotic plaque with very thin fibrous caps, vessel tree, and/or percentage narrowing at different points within the lumen of the blood vessel 102. The structural characteristics, thus determined using high resolution and desired depth-based information, may be used for accurately evaluating a composition of the plaque or other blockages and assessing a pathological condition of the target region. The processing subsystem 100 may then communicate the assessed information to the medical practitioner audibly or visually on the display device 124 for use in providing an accurate diagnosis, prescribing treatment, and/or deploying a vascular stent at the target region of the subject.

Although FIG. 1 illustrates a specific number of exemplary components, in certain embodiments, the system 100 may include fewer or additional components for use in interventional imaging, data processing, and/or for allowing automation of the interventional procedure. In one example, the system 100 may include additional devices such as one or more analog-to-digital-converters (ADC), filters, amplifiers and/or switching subsystems for use in processing acquired or received imaging data. Alternatively, one or more of the components such as the motor controller 108, the processing subsystem 110, the transmit circuitry 114, and/or the receive circuitry 116 may be combined into a single or fewer devices, thus optimizing floor space in the interventional procedure room.

Embodiments of the present system 100, thus, allow for multi-frequency IVUS imaging using a coded and/or extended excitation sequence to drive the broadband transducer 106. The extended excitation sequence allows for increase in total transmitted energy, while maintaining the same peak power without loss in spatial resolution. Specifically, use of the extended excitation sequence improves image penetration at higher frequencies, in turn aiding in accurate evaluation of lumen dimensions, plaque or lesion composition, and information for stent implantation. Additionally, as ultrasound signals are capable of penetrating blood, use of the system 100 minimizes any saline flushing requirements during imaging.

Moreover, use of a single element broadband transducer 106 allows the user to select more than one frequency for driving the transducer 106 for simultaneously acquiring images with desired resolution and penetration. Accordingly, use of the transducer 106 for multi-frequency imaging obviates the need for additional imaging systems or transducers, thereby enhancing the cost-effectiveness of the ultrasound system 100. Moreover, use of the single element broadband transducer 106 allows intrinsic co-registration of the images acquired at different frequencies, thereby preventing any ambiguity while reading the images.

Embodiments of the system 100, thus, provide simultaneous acquisition of high resolution and depth-based information from a target region via use of the coded excitation and the single element broadband transducer 106. Simultaneous availability of both high resolution and depth-based information allows faster and more comprehensive evaluation of the ROI to determine one or more clinically useful indicators representative of a true medical condition of the subject. Certain examples of the structure and functioning of the broadband transducer 106 that allows for efficient multi-frequency ultrasound imaging will be described in greater detail with reference to FIG. 4.

Figure 4:
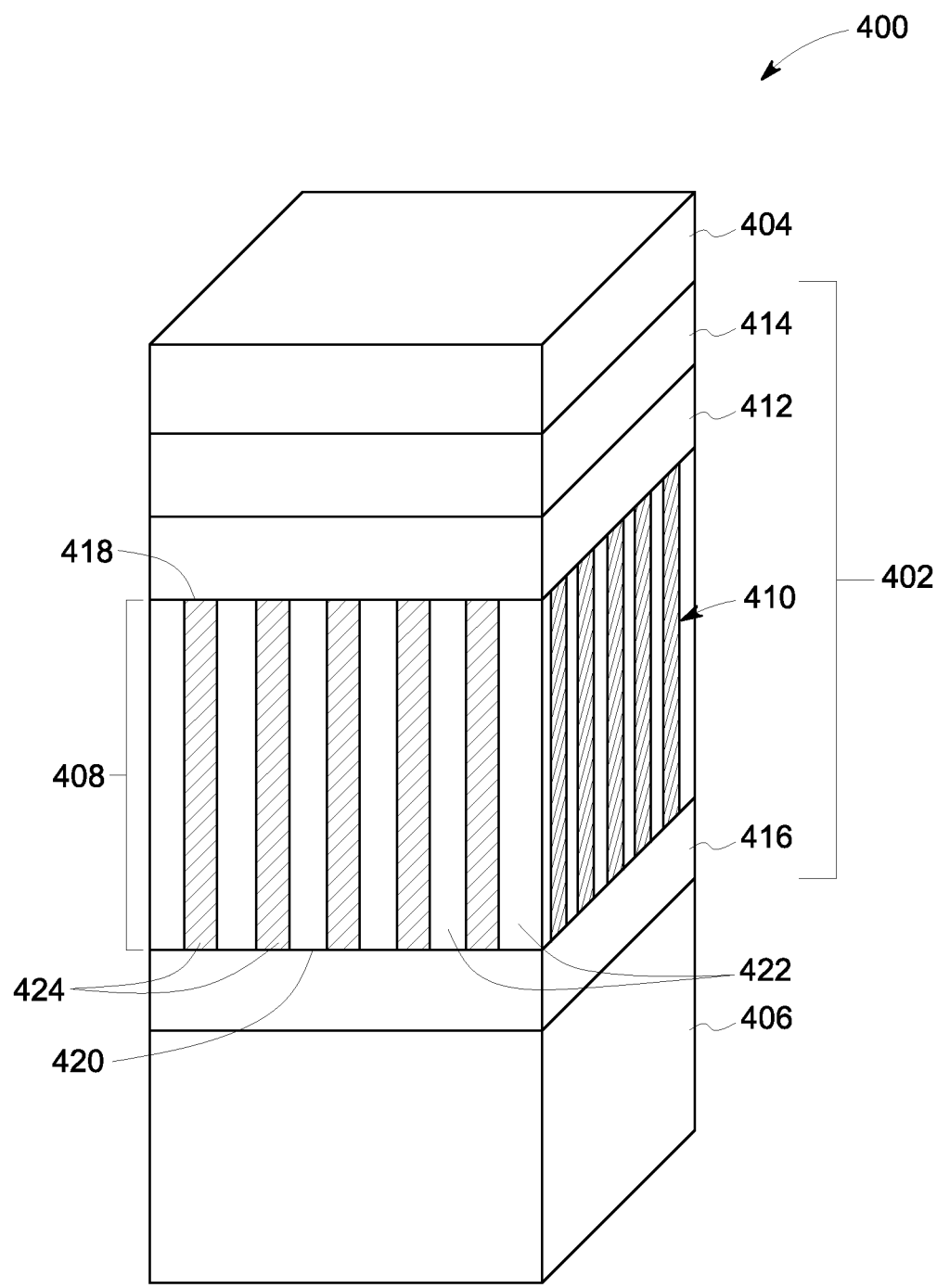
FIG. 4 is a perspective view of an exemplary ultrasound transducer for use in broadband IVUS imaging, in accordance with aspects of the present specification.

FIG. 4 illustrates a perspective view of an exemplary ultrasound transducer 400 for use in broadband ultrasound imaging. For discussion purposes, the transducer 400 is described in the context of an IVUS system. However, certain embodiments of the transducer 400 may be used with any other type of medical and/or non-medical acoustic systems. Particularly, in one embodiment, the transducer 400 includes at least one acoustic element 402, a lens 404, and a backing layer 406 for use in IVUS imaging. In the embodiment illustrated in FIG. 4, the acoustic element 402 is disposed between the lens 404 and the backing layer 406 in a stacked arrangement. However, in alternative embodiments, the transducer 400 may include certain other arrangements of the acoustic element 402, the lens 404, and the backing layer 406 suited for specific imaging and/or packaging scenarios.

Although not shown in FIG. 4, in certain embodiments, the transducer 400 may further include certain additional layers to provide further functionality. In one embodiment, for example, the transducer 400 may include an integrated circuit and/or flex circuit (not shown) configured to provide an electrical connection between the acoustic element 402 and other components of an ultrasound system such as the system 100 of FIG. 1. In another embodiment, the transducer 400 may include a heat sink that is directly or indirectly connected to the backing layer 406 for dissipating heat from the ultrasound transducer 400 that is generated during ultrasound imaging.

According to certain aspects of the present specification, in certain embodiments, the acoustic element 402 is configured to generate, transmit and/or receive ultrasound signals. To that end, in one embodiment, the acoustic element 402 includes an acoustic layer 408 including a micromachined piezoelectric composite body 410. In certain embodiments, the acoustic element 402 may further include one or more other layers such as matching layers 412 and 414, dematching layers 416, and/or conducting layers (not shown) in addition to the acoustic layer 408 including the micromachined piezoelectric composite body 410.

As used herein, the term "micromachined" is used to refer to a composite body formed using a suitable etching process. The etching process, for example, may include reactive ion etching (RIE), deep reactive ion etching (DRIE), laser etching, plasma etching, dry etching, wet etching, and/or photolithography. In certain embodiments, the micromachined piezoelectric composite body 410 includes a front side 418 and a backside 420 that is opposite the front side 418. For discussion purposes, the term "front side" is used herein to refer to a side of the acoustic layer 408 from which ultrasound waves are emitted towards the lens 404. Further, the term "back side" is used herein to refer to a side of the acoustic layer 408 that is positioned opposite the front side 418 and facing away from the lens 404.

In certain embodiments, the micromachined piezoelectric composite body 410 is configured to convert electrical signals into ultrasound waves to be transmitted from the front side 418 of the acoustic layer 408 towards a target to be imaged. The target, for example, may include desired biological tissues in a patient and/or a non-biological object of interest. Furthermore, the micromachined piezoelectric composite body 410 may be configured to receive and convert backscattered acoustic signals from the target into electrical signals for generating corresponding images.

To that end, in certain embodiments, the micromachined piezoelectric composite body 410 includes a plurality of piezoelectric posts 422 that are separated from each other by voids. In one embodiment, the piezoelectric posts 422 may be formed from any piezoelectric substance, such as, but not limited to, a crystalline, amorphous, and/or ceramic piezoelectric material. Furthermore, piezoelectric substances having different structures, dielectric constants, and/or dielectric losses may be used to form the piezoelectric posts 422. By way of example, the piezoelectric posts 422 may be formed from lead magnesium niobate-lead titanate (PMN-PT), lead zinc niobate-lead titanate (PZN-PT), lead zirconate titanate (PZT), PIN-PMN-PT, and/or the like.

Further, the voids may include one or more filler members 424 such as a polymer, an epoxy, and/or other suitable material. In one example, the filler members 424 may include substances such as Epo-Tek-301 (commercially available from Epoxy Technology, Inc. of Billerica, Mass.), Epo-Tek-301-2 (commercially available from Epoxy Technology, Inc. of Billerica, Mass.), and/or the like. As a composition of the filler members 424 is typically different from that of the piezoelectric posts 422, the micromachined piezoelectric body 410 is referred to herein as a "composite" body.

Moreover, according to certain exemplary aspects of the present specification, the piezoelectric posts 422, the voids, and/or filler members 424 may have any size and any shape. Particularly, in the embodiment illustrated in FIG. 4, all the piezoelectric posts 422 are depicted as parallelepipeds. However, in an alternative embodiment, one or more of the piezoelectric posts 422, voids, and filler members 424 may additionally or alternatively include one or more sizes (height, width, and/or thickness) and/or one or more shapes, such as, but not limited to, a triangular, circular, oval, curved, octagonal, and/or star shape.

Additionally, an arrangement of the piezoelectric posts 422 and the filler members 424 may not be limited to a grid-like pattern shown in the embodiment depicted in FIG. 4. Rather, in alternative embodiments, the piezoelectric posts 422 and the filler members 424 may be arranged in any other pattern relative to each other. For example, the voids and/or the filler members 424 may have any size such that the piezoelectric posts 422 may be spaced apart by different desired amounts, which may or may not be consistent throughout the pattern of the piezoelectric posts 422 and the filler members 424. Furthermore, a perimeter of the micromachined piezoelectric body 410 may be square, rectangle, triangular, oval, circular, curved, and/or star-shaped to suit different ultrasound application requirements. For example, a circular and/or other curved shaped array of the piezoelectric posts 422 and the filler members 424 in the micromachined piezoelectric body 410 may be disposed in forward facing position in an imaging catheter and/or on a guide wire to allow for efficient IVUS imaging.

Typically, the piezoelectric body 410 has a much higher acoustic impedance (Z) than the target being imaged. If the piezoelectric body 410 were to be used by itself during imaging, the large impedance mismatch between the piezoelectric body 410 and the target would result in significant loss of acoustic energy. Accordingly, in certain embodiments, the acoustic element 402 includes one or more matching layers 412 and 414 positioned between the piezoelectric body 410 and the lens 404 or a face layer of the transducer 400.

In one embodiment, the matching layers 412 and 414 have acoustic impedances that are less than the acoustic impedance of the acoustic layer 408 to reduce the loss of acoustic energy. In certain embodiments, the plurality of the matching layers 412 and 414 may be selected to provide a progressive reduction in acoustic impedance relative to the acoustic layer 408. Optionally, each of the matching layers 412 and 414 may have a relatively high thermal conductivity, for example, greater than about 30 watts per meter per kelvin (W/mK). Accordingly, use of the matching layers 412 and 414 may result in less reflection and/or refraction of ultrasound waves between the acoustic layer 408 and the lens 404. More specifically, use the matching layers 412 and 414 may allow for an impedance transition from the piezoelectric body 410 to the lens 404

Thus, in certain embodiments, each of the matching layers 412 and 414 may have the same or different thicknesses. In one embodiment, for example, the matching layers 412 and 414 may have a combined thickness of approximately $\frac{1}{4}^{th}$ or less of a wavelength at the resonant frequency of the ultrasound transducer 400. Such a thickness of the matching layers 412 and 414 may minimize destructive interference caused by waves reflected from the boundaries between each of the matching layers 412 and 414. Additionally, each of the matching layers 412 and 414 may include materials such as a filled epoxy including one or more fillers, metal-impregnated graphite, glass ceramic, composite ceramic, and/or metal (such as, but not limited to, copper, copper alloy, copper with graphite pattern embedded therein, magnesium, magnesium alloy, aluminum, and/or aluminum alloy). By way of example, in the embodiment illustrated in FIG. 4, the transducer 400 may include an inner matching layer 412 formed of silver particle loaded epoxy and an outer matching layer 414 formed of parylene.

Furthermore, in certain embodiments, each of the matching layers 412 and 414 may be electrically conductive. In other embodiments, the matching layers 412 and 414 may be electrically non-conductive. When the matching layers 412 and 414 are electrically non-conductive, one or more of the matching layers 412 and 414 optionally include a conductive film layer (not shown) thereon to provide an electrical ground connection for the acoustic element 402. Particularly, in one embodiment, the matching layers 412 and 414 may be configured to directly connect (for example, via direct physical contact) the lens 404 to the front side 418 of the acoustic layer 408. In an alternative embodiment, however, the matching layers 412 and 414 may be configured to indirectly connect the lens 404 to the front side 418 of the micromachined piezoelectric composite body 410. Further, in certain embodiments, the matching layers 412 and 414, the acoustic layer 408, and/or the lens 404 may be bonded together using epoxy and/or other adhesive material. For example, the bonding may be achieved by using a material cured under pressure and supplied by tooling including a press machine and/or the like to allow for optimal impedance matching during imaging.

Additionally, in certain embodiments, the transducer 400 includes at least one dematching layer 416 having an acoustic impedance that is higher than the acoustic impedance of the acoustic layer 408 to increase the power of the ultrasound waves transmitted to the lens 404. In other words, the dematching layer 416 may be selected to have a higher acoustic impedance than the micromachined piezoelectric composite body 410 of the acoustic layer 408. Particularly, the relatively high acoustic impedance (for example at least approximately 39 MegaRayls (MRayls)) of the dematching layer 416 may allow a majority of the acoustic energy to be transmitted out through the front side 418 of the acoustic layer 408, thereby aiding the transducer 400 in providing broadband imaging functionality.

To that end, in one embodiment, the dematching layer 416 is disposed between the backing layer 406 and the backside 420 of the acoustic layer 408. In the embodiment illustrated in FIG. 4, the dematching layer 416 is directly connected to (that is in direct physical contact with) the backside 420 of the acoustic layer 408. However, in an alternative embodiment, the dematching layer 416 may be indirectly connected to the backside 420 of the acoustic layer 408 through one or more additional structures and/or components. For example, the dematching layer 416 may be bonded with the acoustic layer 408 using epoxy and/or other adhesive material, such as, but not limited to, a material cured under pressure and supplied by tooling including a press machine and/or the like.

Furthermore, the dematching layer 416 may include a metal, carbide alloy, and/or a compound material. Specifically, in one embodiment, the dematching layer 416, for example, may include zirconium, tungsten carbide, silicon, titanium, tantalum carbide, and/or the like. Each dematching layer 416 may have any desired thickness and, in embodiments where a plurality of dematching layers 416 are provided, the dematching layers 416 may have any combined thickness. Particularly, the thickness of one or more dematching layers 416 may be selected based on a frequency of the ultrasound transducer 400. Examples of the thickness of a dematching layer 416 include, but are not limited to, between approximately 49 micrometer and approximately 351 micrometer. Moreover, in certain embodiments, the dematching layer 416 may be laminated to the acoustic layer 408 using any suitable method, structure, process, means, and/or the like. On example of a lamination process may include using epoxy having an exemplary thickness of less than approximately 5 micrometer.

Additionally, in one embodiment, the dematching layer 416 is coated with an electrically conductive coating (not shown), for example a metal coating, to facilitate electrical connection between the dematching layer 34 and one or more other components of the ultrasound transducer 400. In certain embodiments, the acoustic element 402 may additionally or alternatively be provided with electrical contacts (not shown) such as solder pads, solder bumps, stud bumps, plated bumps to allow for electrical connection with other components.

Although, the embodiment illustrated in FIG. 4 depicts only a single dematching layer 416, in alternative embodiments, the acoustic element 402 may include any number of dematching layers 416. Each dematching layer 416 may have any value of acoustic impedance, such as, but not limited to, at least approximately 40 MRayls, or between approximately 39 MRayls and approximately 121 MRayls. Moreover, the dematching layer 416 may have relatively good thermal conductivity to transfer the heat generated by the acoustic layer 408 to the backing layer 406.

However, a small amount of backside acoustic energy may still be reflected back to the front side 418, thereby causing artifacts in images generated from ultrasound signals acquired by the transducer 400. Accordingly, in one embodiment, the transducer 400 may include the backing layer 406 fabricated from a relatively high acoustic attenuation material to dampen the backside acoustic energy, thereby reducing acoustic reverberation inside the ultrasound transducer 400. For example, the backing layer 18 may be fabricated from an epoxy with a filler material such as, but not limited to, titanium dioxide and/or the like. Moreover, the backing layer 406 may have any thickness, such as approximately from 1 millimeter (mm) to approximately 20 mm. In certain embodiments, the backing layer 406, in conjunction with the dematching layer 416, allows the ultrasound transducer 400 to transmit more energy in the forward direction, thereby allowing for broadband imaging operation.

Typically, the imaging resolution of an ultrasound transducer is inversely proportional to its frequency bandwidth. Accordingly, a transducer with a relatively broad bandwidth is able to generate relatively short ultrasonic pulses, which may facilitate distinguishing close targets in an axial direction. However, the bandwidth of the transducer may be affected by various parameters such as acoustic matching schemes of the transducer, an electromechanical coupling coefficient (kt), piezoelectric coefficient (dt), and/or acoustic impedance of an acoustic layer in the transducer.

Accordingly, embodiments of the transducer 400 include the micromachined piezoelectric composite body 410 having a relatively high electromechanical coupling coefficient kt (for example, at least approximately 0.7) and a relatively low acoustic impedance (for example, less than approximately 36 MRayls). The relatively high electromagnetic coupling coefficient kt of the micromachined piezoelectric composite body 410 allows for efficient conversion of mechanical energy to electrical energy, and vice versa, thereby facilitating both transmitting and receiving ultrasonic waves. Further, the relatively low acoustic impedance of the micromachined piezoelectric composite body 410 as compared to the dematching layer 416 allows for efficiently propagating acoustic energy between a loading medium such as water and the transducer 400. The efficient propagation of the acoustic energy, in turn, enhances the sensitivity and/or bandwidth of the transducer 400 by reducing the acoustic reverberation inside the transducer 400.

Furthermore, according to certain aspects of the present specification, the relatively high frequency and/or the increased bandwidth of the ultrasound transducer 400 allows for greater imaging resolution and/or image depth. For example, the transducer 400 may provide broad frequency response covering about 35-85 MHz (−6 dB) or 15-120 MHz (−40 dB). The transducer 400, thus, may facilitate multi-frequency IVUS imaging, for example, at about 40 MHz, about 60 MHz, and/or about 80 MHz, thus allowing for generation and display of two or more IVUS images of the same vessel cross section simultaneously at different frequencies.

Consequently, the broadband ultrasound transducer 400 may provide improved axial resolution during IVUS imaging. The improved imaging resolution may be beneficial for identifying microstructures of atherosclerotic plaques. Moreover, the relatively low acoustic impedance of the acoustic layer 408 (specifically the body 410) and the relatively high acoustic impedance of the dematching layer 416 may provide the ultrasound transducer 10 with improved sensitivity. Such an improved sensitivity may be beneficial for enabling ultrasound waves to penetrate through blood and into a vessel wall, which may increase the dynamic range and/or penetration depth of the ultrasound transducer 400.

However, merely substituting the transducer 400 for a conventional transducer in a conventional ultrasound imaging system may not allow for optimal use of the broadband capabilities of the transducer 400. Particularly, conventional ultrasound signal processing procedures may not be able to leverage the multiple frequency imaging capabilities of the broadband transducer 400. As the conventional ultrasound signal processing procedures may continue to process the acquired ultrasound signals at a single frequency, the conventional signal processing procedures may not be able to generate and display two or more IVUS images of the same vessel cross section simultaneously at different frequencies.

In contrast, embodiments of the present specification disclose an efficient signal processing method that employs coded excitation to leverage the multi-frequency imaging capabilities of the ultrasound transducer 400 for simultaneously providing images with higher resolution and greater depth. An embodiment of the method employing coded excitation is discussed in greater detail with reference to FIG. 5.

Figure 5:
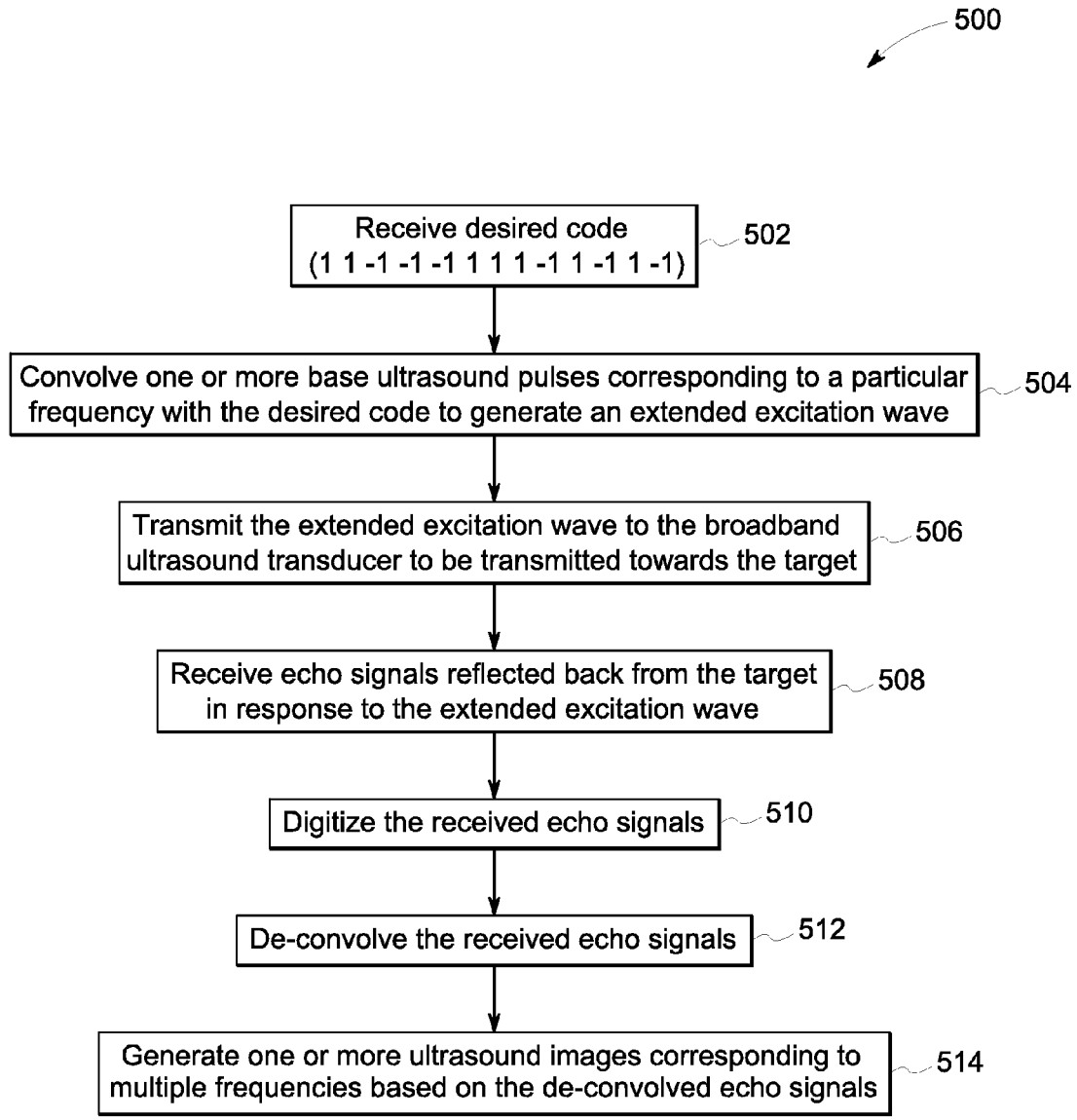
FIG. 5 is a flow diagram illustrating an exemplary method for broadband IVUS imaging using coded excitation, in accordance with aspects of the present specification.

FIG. 5 illustrates a flow chart 500 depicting an exemplary method for multi-frequency ultrasound imaging. The exemplary method may be described in a general context of computer executable instructions stored and/or executed on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 5, the exemplary method is illustrated as a collection of blocks in a logical flow chart, which represents operations that may be implemented in hardware, software, or combinations thereof. The various operations are depicted in the blocks to illustrate the functions that are performed, for example, during the steps of convolving base ultrasound pulses using a desired code, de-convolving received echo signals, and generating ultrasound images corresponding to multiple frequencies in the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-4.

As previously noted, conventional IVUS systems employ only single or two cycles of excitation pulses for imaging a target feature at a single frequency. However, use of the conventional excitation pulses having a single frequency may fail to provide sufficient image resolution and penetration depth simultaneously in the same or different images. Accordingly, embodiments of the present method employ a coded excitation sequence to leverage the multi-frequency IVUS imaging capability of a broadband transducer, such as the transducer 106 of FIG. 1 and/or the transducer 400 of FIG. 4.

It may be noted that although coded excitation has been used in RADAR and SONAR applications, coded excitation of a conventional IVUS transducer results in unacceptably high-range side lobes due to limited bandwidth. Thus, coded excitation is typically unfeasible for use in conventional low-bandwidth IVUS imaging. In contrast, use of coded excitation with an embodiment of the broadband transducer 106 or 400 of FIG. 1 or 4 significantly improves the SNR ratio without either increasing a peak transmitted power or sacrificing resolution of resulting ultrasound images.

Accordingly, at step 502, one or more desired codes may be received. In certain embodiments, the desired code may be received from a user, or may be selected from a plurality of codes stored in a storage repository such as the storage device 120 of FIG. 1. Particularly, in one embodiment, the desired code may be retrieved from the storage repository based on a stored correlation. The stored correlation may correspond to a determined association between the desired code, imaging requirements at the time, structural characteristics of the target, and/or operating specifications of the broadband transducer. For example, a specific code may be designed and stored as a correlation in the storage repository to optimally image a liver of an obese adult male patient when using a particular broadband transducer and specific ultrasound system settings. In certain embodiments, in addition to the desired code, a center frequency of the base ultrasound pulses, a number of cycles of the base ultrasound pulses, and/or a number of bits of the desired code may also be determined based on the stored correlation.

Further, at step 504, one or more base ultrasound pulses corresponding to a particular frequency may be convolved with the desired code to generate an extended excitation wave. In one embodiment, for example, one, two, or more cycles of sinusoidal, square, sawtooth, and/or triangular waves at one or more frequencies, may be encoded using the desired code and/or a desired sequence of codes. Specifically, one or more cycles of the base excitation pulses may be combined and/or may undergo a change in phase to generate an extended excitation pulse that embeds the desired code.

In certain embodiments, the extended excitation pulse may be generated in single and/or tone bursts and may be unipolar, bipolar, and/or arbitrary pulses having application-defined or user-defined duration and/or frequency. Further, at step 506, the extended excitation wave is transmitted to the broadband ultrasound transducer to be transmitted towards the target. Particularly, the extended excitation pulse may be used to drive the broadband transducer at multiple frequency bands, for example at about 40 MHz, 60 MHz, and/or 80 MHz, for imaging a target region such as a suspected atherosclerotic lesion.

In one embodiment, at least a portion of the extended excitation signal is reflected back from the target region to the broadband ultrasound transducer. Accordingly, at step 508, the echo signals reflected back from the target in response to the extended excitation wave are received. Further, at step 510, the received echo signals may be digitized. Specifically, the broadband ultrasound transducer may be configured to convert the reflected ultrasound signals into electrical signals for further processing. For example, the received echo signals may be pre-amplified and digitized for use in determining clinically useful indicators.

Further, at step 512, the received echo signals may be de-convolved. In particular, the received echo signals may be de-convolved or decoded to recover an original resolution of the transducer 106 at different frequencies. Subsequently, at step 514, one or more ultrasound images corresponding to multiple frequencies may be generated based on the de-convolved echo signals. Specifically, the de-convolved echo signals may be processed at the multiple frequencies to reconstruct multiple 2D and/or a 3D cross-sectional image of the target region at the different resolutions and desired penetration depths.

In certain other embodiments, these multi-frequency 2D and/or 3D images may be displayed along with clinically useful information such as patient data on a display device, such as the display device 124 of FIG. 1. Particularly, in one embodiment, the multi-frequency 2D and/or 3D images that are reconstructed from the same set of received signals and are indicative of high resolution and desired depth-based information may be simultaneously displayed on the display device. In a further embodiment, the multi-frequency 2D and/or 3D images and the clinically useful information may be stored for later review and analysis, and/or may be communicated to a remotely located medical practitioner for further evaluation.

In certain embodiments, the multi-frequency 2D and/or 3D images including the high resolution and desired depth-based information may be used for determining structural characteristics corresponding to the target region with greater accuracy. For example, the multi-frequency images may be used to identify locations and tissue morphology of an atherosclerotic plaque with very thin fibrous caps, vessel tree, and/or percentage narrowing at different points within the lumen of the blood vessel. The structural characteristics, thus determined using high resolution and desired depth-based information, may be used for accurately evaluating a composition of the plaque or other blockages and assessing a pathological condition of the target region. The assessed information may then be communicated to the medical practitioner audibly or visually on the display device for use in providing an accurate diagnosis, prescribing treatment, and/or deploying a vascular stent at the target region of the subject.

Embodiments of the present method, thus, allow for multi-frequency IVUS imaging using a coded and/or extended excitation sequence to drive the broadband transducer. The extended excitation sequence allows for increase in total transmitted energy, while maintaining the same peak power without loss in spatial resolution. Specifically, use of the extended excitation sequence improves image penetration at higher frequencies, in turn aiding in accurate evaluation of lumen dimensions, plaque or lesion composition, and information for stent implantation.

Furthermore, use one single element broadband transducer allows the user to select more than one frequency for driving the broadband transducer for simultaneously acquiring images with desired resolution and penetration. Accordingly, use of the broadband transducer for multi-frequency imaging obviates the need for additional imaging systems or transducers, thereby enhancing the cost-effectiveness of the present ultrasound system. Moreover, use of the single element broadband transducer allows intrinsic co-registration of the images acquired at different frequencies, thereby preventing any ambiguity while reading the images.

Embodiments of the present system and method, thus, provide simultaneous acquisition of high resolution and depth-based information from a target region via use of the coded excitation and the single element broadband transducer. Simultaneous availability of both high resolution and depth-based information allows faster and more comprehensive evaluation of the target region to determine one or more clinically useful indicators representative of a true medical condition of the subject.

It may be noted that although specific features of various embodiments of the present systems and methods may be shown in and/or described with respect to only certain drawings and not in others, this is for convenience only. It is to be understood that the described features, structures, and/or characteristics may be combined and/or used interchangeably in any suitable manner in the various embodiments, for example, to construct additional assemblies and techniques. Furthermore, the foregoing examples, demonstrations, and process steps, for example, those that may be performed by the motor controller 108 and the processing subsystem 110 may be implemented by a single device or a plurality of devices using suitable code on a processor-based system.

It should also be noted that different implementations of the present specification may perform some or all of the steps described herein in different orders or substantially concurrently, that is, in parallel. In addition, the functions may be implemented in a variety of programming languages, including but not limited to Python, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by a processor-based system to execute the stored code.

While only certain features of the present specification have been illustrated and described herein, many modifications and changes will occur to those skilled in the art. It is, therefore, to be understood that the appended claims are intended to cover all such modifications and changes as fall within the true spirit of the present specification.

The invention claimed is:

1. A broadband intravascular ultrasound imaging system, comprising:
a broadband ultrasound transducer configured to transmit ultrasound pulses towards a target, wherein the broadband ultrasound transducer comprises a micromachined piezoelectric composite body having a front side and a back side opposite to the front side, wherein the micromachined piezoelectric composite body is configured to convert electrical signals into ultrasound waves to be transmitted from the front side toward the target, and wherein the micromachined piezoelectric composite body is configured to convert the received echo signals into electrical signals, the micromachined piezoelectric composite body including a plurality of piezoelectric posts separated from each other by a plurality of filler members; and a dematching layer connected to the back side of the micromachined piezoelectric composite body and having higher acoustic impedance than an acoustic impedance of the micromachined piezoelectric composite body, the dematching layer not including the plurality of piezoelectric posts and the plurality of filler members; and a processing subsystem operatively coupled to the broadband ultrasound transducer and configured to:

convolve one or more base ultrasound pulses corresponding to a particular frequency with a desired code to generate an extended excitation wave for driving the broadband transducer at a plurality of different frequencies;

transmit the extended excitation wave to the broadband ultrasound transducer to be transmitted towards the target;

receive echo signals reflected back from the target in response to the extended excitation wave;

de-convolve the received echo signals to recover an original resolution of the broadband ultrasound transducer at the plurality of different frequencies; and generate a plurality of ultrasound images of the target corresponding to each of the plurality of different frequencies based on the de-convolved echo signals.

2. The system of claim 1, wherein the processing subsystem is configured to receive the desired code from a user, a storage repository, or a combination thereof.

3. The system of claim 1, wherein the processing subsystem is configured to select a center frequency of the base ultrasound pulses, a number of cycles of the base ultrasound pulses, a number of bits of the desired code, or combinations thereof, based on user input, a stored correlation, or a combination thereof.

4. The system of claim 1, further comprising a display device configured to simultaneously display the plurality of ultrasound images corresponding to each of the plurality of different frequencies.

5. The system of claim 1, wherein the broadband ultrasound transducer is a single element transducer disposed at one end of an intravascular ultrasound device.

6. The system of claim 1, wherein the ultrasound imaging system is a non-destructive evaluation system.

7. A method for a broadband intravascular ultrasound imaging system comprising a processing subsystem operatively coupled to a broadband ultrasound transducer, the method comprising:

convolving one or more base ultrasound pulses corresponding to a particular frequency with a desired code to generate an extended excitation wave for driving the broadband transducer at a plurality of different frequencies;

transmitting the extended excitation wave to a broadband ultrasound transducer to be transmitted towards the target, the broadband ultrasound transducer comprising a micromachined piezoelectric composite body having a front side and a back side opposite to the front side, wherein the micromachined piezoelectric composite body is configured to convert electrical signals into ultrasound waves to be transmitted from the front side toward the target, and wherein the micromachined piezoelectric composite body is configured to convert the received echo signals into electrical signals, the micromachined piezoelectric composite body including a plurality of piezoelectric posts separated from each other by a plurality of filler members; and a dematching layer connected to the back side of the micromachined piezoelectric composite body and having higher acoustic impedance than an acoustic impedance of the micromachined piezoelectric composite body, the dematching layer not including the plurality of piezoelectric posts and the plurality of filler members;

receiving echo signals reflected back from the target in response to the extended excitation wave;

de-convolving the received echo signals to recover an original resolution of the broadband ultrasound transducer at the plurality of different frequencies; and generating a plurality of ultrasound images of the target corresponding to each of the plurality of different frequencies based on the de-convolved echo signals.

8. The method of claim 7, further comprising receiving the desired code from a user, a storage repository, or a combination thereof.

9. The method of claim 8, further comprising designing the desired code based on imaging requirements, structural characteristics of the target, operating specifications of the broadband transducer, or combinations thereof.

10. The method of claim 8, wherein receiving the desired code comprises retrieving the desired code from a storage repository based on a stored correlation between one or more imaging parameters and one or more desired image quality tradeoffs corresponding to a particular imaging application.

11. The method of claim 9, wherein retrieving the desired code comprises selecting the desired code from a plurality of codes from the storage repository.

12. The method of claim 7, further comprising selecting a center frequency of the base ultrasound pulses, a number of cycles of the base ultrasound pulses, a number of bits of the desired code, or combinations thereof, based on user input, imaging requirements, structural characteristics of the target, operating specifications of the broadband transducer, or a combination thereof.

13. The method of claim 7, further comprising simultaneously displaying the plurality of ultrasound images corresponding to each of the plurality of different frequencies on a display device.

14. The method of claim 7, wherein convolving the one or more base ultrasound pulses comprises encoding one or more cycles of sinusoidal waves to generate the extended excitation wave.

15. The method of claim 7, wherein convolving the one or more base ultrasound pulses comprises encoding one or more cycles of sinusoidal waves, square waves, sawtooth-shaped waves, triangular waves, or combinations thereof, using more than one desired code to generate the extended excitation wave.

16. The method of claim 7, wherein convolving the one or more base ultrasound pulses comprises encoding one or more cycles of the base ultrasound pulses using a desired sequence of codes.

17. The method of claim 7, further comprising providing an assessment of the target based on the ultrasound images of the target corresponding to multiple frequencies.

18. The method of claim 7, wherein providing an assessment of the target comprises identifying microstructures of atherosclerotic plaques in the target, wherein the target is a person.

19. A non-transitory computer readable medium that stores instructions executable by a broadband intravascular ultrasonic imaging system comprising a broadband ultrasound transducer coupled to one or more processors to perform a method for ultrasound imaging, the non-transitory computer readable medium configured to:

convolve one or more base ultrasound pulses corresponding to a particular frequency with a desired code to generate an extended excitation wave for driving the broadband transducer at a plurality of different frequencies;

transmit the extended excitation wave to a broadband ultrasound transducer to be transmitted towards the target, the broadband ultrasonic transducer comprising a micromachined piezoelectric composite body having a front side and a back side opposite to the front side, wherein the micromachined piezoelectric composite body is configured to convert electrical signals into ultrasound waves to be transmitted from the front side toward the target, and wherein the micromachined piezoelectric composite body is configured to convert the received echo signals into electrical signals, the micromachined piezoelectric composite body including a plurality of piezoelectric posts separated from each other by a plurality of filler members; and a dematching layer connected to the back side of the micromachined piezoelectric composite body and having higher acoustic impedance than an acoustic impedance of the micromachined piezoelectric composite body, the dematching layer not including the plurality of piezoelectric posts and the plurality of filler members;

receive echo signals reflected back from the target in response to the extended excitation wave;

de-convolve the received echo signals to recover an original resolution of the broadband ultrasound transducer at the plurality of different frequencies; and generate a plurality of ultrasound images of the target corresponding to each of the plurality of different frequencies based on the de-convolved echo signals.

* * * * *